(12) United States Patent
Fukunishi et al.

(10) Patent No.: US 6,337,357 B1
(45) Date of Patent: Jan. 8, 2002

(54) ANTIMICROBIAL CARIES-DETECTING COMPOSITION

(75) Inventors: Kyoko Fukunishi; Kenichi Hino, both of Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/493,153

(22) Filed: Jan. 28, 2000

Related U.S. Application Data

(62) Division of application No. 09/028,671, filed on Feb. 24, 1998, now Pat. No. 6,084,005.

(30) Foreign Application Priority Data

Feb. 24, 1997 (JP) ............................................... 9-38681
Feb. 27, 1997 (JP) ............................................... 9-45634

(51) Int. Cl.⁷ .............................................. A61K 6/083
(52) U.S. Cl. ........................ 523/122; 427/2.13; 424/49; 433/217.1; 523/105; 106/35
(58) Field of Search ........................ 424/49; 433/217.1; 427/2.13; 523/122, 105; 106/35

(56) References Cited

U.S. PATENT DOCUMENTS

| | | | | |
|---|---|---|---|---|
| 4,348,378 A | * | 9/1982 | Kosti ........................... | 424/49 |
| 4,565,691 A | * | 1/1986 | Jackson ........................ | 424/49 |
| 4,992,256 A | * | 2/1991 | Skaggs et al. ................. | 424/49 |
| 5,026,539 A | * | 6/1991 | Jackson et al. ................ | 424/49 |
| 5,211,940 A | * | 5/1993 | Ishiguro et al. ................ | 424/49 |
| 5,401,496 A | * | 3/1995 | Fitzig et al. ................... | 424/49 |
| 5,408,022 A | | 4/1995 | Imazato et al. | |
| 5,494,987 A | | 2/1996 | Imazato et al. ........................ | |

* cited by examiner

*Primary Examiner*—Peter Szekely
(74) *Attorney, Agent, or Firm*—Oblon, Spivak, McClelland, Maier & Neustadt, P.C.

(57) ABSTRACT

An antimicrobial caries-detecting composition, which comprises (i) water, a water-miscible solvent or a combination thereof, (ii) a dye capable of staining the caries-infected portions of teeth, and (iii) at least one antimicrobial agent.

6 Claims, No Drawings

ANTIMICROBIAL CARIES-DETECTING COMPOSITION

This application is a division of U.S. application No. 09/028,671, filed Feb. 29, 1998, now U.S. Pat. No. 6,084,005.

BACKGROUND OF THE INVENTION

1. Field of the Invention

The present invention relates to an antimicrobial caries detecting composition for use in the odontological treatment of caries-infected teeth, which composition selectively stains the portion of a tooth which is infected with cariogenic microbes, prior to removal of the infected dentin of the tooth, thereby facilitating the removal of the infected portion of the tooth. More particularly, the present invention relates to a composition which is capable of sterilizing and staining the infected portions of teeth at the same time.

2. Description of the Background

In the conventional treatment of tooth caries which removes the dentin infected with cariogenic microbes, the infected portion is selectively stained so as to clearly differentiate the infection from the non-infected portions, thereby removing the infected dentin as completely as possible. In order to achieve this objective, Japanese Patent Application (JPA) Kokai No. Sho-51-38428 discloses a "caries-detecting composition" which comprises a basic fuchsine and a mono- or polyalcohol, and shows some effectiveness. However, even with the development of such a caries-detecting composition and its wide-spread commercial use, there is still no end to the reports of pulp irritation after caries treatment, which is a serious problem in the field of dentistry.

On the other hand, in order to prevent caries, JPA Kokai No. Sho-51-38427 discloses as its objective, a "dental plaque or calculus-detecting composition", which is used to stain the dental plaque or the like which adheres to the tooth surface thereby causing caries. JPA Kokai No. Sho-56-96700 discloses a "caries activity-indicating composition", which is used with sufficient daily teeth brushing and thereby provides an evaluation of the degree of danger of dental plaque. The former composition comprises a dye which is dissolved in a polyalcohol and/or water, while the latter composition comprises a pH indicator which is dissolved in an aqueous solution of a water-soluble polymer to which is added an antibiotic or preservative selected from chloraphenicol compounds and sodium azide compounds.

The cause of the dental pulp irritation, which has been discussed in those proposals, most probably is attributable to the penetration of the restorative component into the dental pulp. Various studies have been made on this penetration. However, it has been found that even if the restorative component itself is embedded adjacent to dental pulp, no serious irritation results. In this regard it has been recently proposed, as a component of the theory of bacterial cariogenesis, that the secondary invasion of oral bacteria into a cavity and the failure to remove the carcinogenic microbe-infected portion of a tooth, causes dental pulp irritation. In fact, recent studies into the prevention of secondary invasions of oral bacteria into cavities have been directed to increasing the adhesiveness between the dental pulp and the restorative material applied thereto in order to improve the sealing the margin of the restorative material. As a result, recent advances have achieved a very high level of adhesion between the dentin and the restorative material. Accordingly, cases of dental pulp irritation have decreased in recent days. However, it can not be said that there have been no reports of dental pulp irritation after caries treatment.

The cause of dental pulp irritation which appears to remain is the failure to remove all of the caries-infected dentin and the contamination of cleaned cavity with caries-infected tissue pieces that have just been removed from the cavity before the application of a restorative material thereto.

In the work leading to the present invention, the present inventors have assiduously studied various materials which would enable the complete removal of the cariogenic microbes-infected portions from teeth and/or elimination of the contamination by the once-removed infected dentin from the cleaned cavity. The following has been found.

(1) A caries-detecting composition can not completely penetrate into the deepest portion of the caries-infected portion of teeth by one application, if the infected portion is thick. Therefore, a dentist repeatedly applies the caries-detecting composition to the affected area of a tooth to confirm the infected part, and then bores a cavity in the affected part. However, if the dentist has failed to finally stain the infected portion in the last test for infected matter, it is probable that cariogenic microbes have not been completely removed.

(2) At the point at which the removal of the infected dentin is almost finished, it is often difficult to determine whether or not the dentin had been stained, so that removal of the infected dentin is often incomplete. In the case the cavity bottom is too thin, the cutting tool used would often penetrate the dental pulp. In order to prevent this problem, the operating dentist would often stop the removal of the seemingly slightly stained part.

(3) A so-called smear layer comprising powdered dentin is inevitably formed on the surface of the dentin from which the infected portion has been removed. It is likely that bacteria will remain in the smear layer.

(4) Since dentinal tubules are found in the surface of the dentin which has been drilled for the removal of the infected portion of the tooth, the smear layer is pressed into the dentinal tubules thereby forming a plug. It is said that the smear plug remaining in the opening of the dentinal tubules has an important role in protecting dental pulp from the components of restorative materials. It is likely, however, that the plug may be infected with cariogenic microbes.

(5) Another possible source of contamination is the highly-contaminated dentin pieces which are scattered around the infected tooth during removal of the infected portion. This material is mixed with body fluids such as saliva, and likely again contaminates the affected portion. No attempts have been made to solve the possible problem of item (5).

The failure to remove any infected dentin must be solved. However, even if the infected dentin can not be completely removed or even if the infected dentin contaminates the affected portion, such should not cause cariogenesis if the bacteria existing in the infected dentin are inactivated. In order to achieve inactivation, if the cavity formed in an infected tooth is treated with a microbiocidal solution which is effective against cariogenic microbes, the object of the invention can be attained. Some trial reports have been introduced at various meetings of dental societies and in various odontological journals. However, even if carious cavities are treated with a microbiocidal solution, the question of whether or not the microbiocidal solution penetrates throughout the entire region of the infected dentin depends on the thickness of the infected dentin. The pulp cavity has its own inner pressure, and the inner fluid in dentinal tubules flows from the pulp to the surface of the tooth. Therefore, even if a microbiocide is applied to the surface of the infected dentin, it is in fact difficult for the microbiocide to effectively penetrate into the inner depth of the infected dentin. Accordingly, if the infected dentin is thick, it is likely that the microbiocide applied thereto is often ineffective. After having made repeated studies to solve the above-mentioned problems, the present inventors have reached the following conclusions:

(1) When a caries-detecting composition is used to stain infected dentin while simultaneously sterilizing the dentin, the powdered dentin formed during a subsequent step of removing the dentin is sterilized. Therefore, the danger of dental pulp irritation, because of contamination of the powdered dentin in the affected portion, is greatly reduced, and even the danger of contamination of the adjacent teeth and the gums is reduced. Further, the possibility of infection from the tools that may induce additional cariogenesis is also greatly reduced.

(2) Where the infected dentin is removed and is simultaneously stained for caries detection and sterilization, the infected dentin is well-sterilized while its thickness is reduced. Here, even the bacteria existing in the depths of the affected portions can be effectively killed. In particular, after the last staining for the final confirmation, no infected dentin exists in the cavity. Even if some bacteria have readhered to the affected portions, they shall be completely free of bacteria. Under these conditions, therefore, satisfactory treatment is ensured. On the basis of these findings, the present inventors have made the following studies in order to find an antimicrobial caries-detecting composition.

The microbiocide which is employed in the present invention may be any and every known type that has been used in detergents and microbicidal compositions for dental use. However, (1) preferred microbiocides are those which are capable of killing 99% or more of 10 thousands of bacteria per 1 cm$^3$ with a solution having a microbicidal concentration of 1000 μg/ml for 10 seconds, wherein said bacteria include Mutans streptococci I and Lactobaclli, which are said to be cariogenic bacteria, *Streptococcus mitis*, and *Actinomyces viscosus*, which are said to be bacteria that may have cariogenicity, and strictly anaerobic bacterias which are said to cause dental pulp irritation.

(2) The microbiocides must be soluble in water and/or water-miscible solvents.

(3) When stored in the composition of the invention, the microbicides must be stable for a long period of time, and must not discolor the dye which is essential to the composition.

Among conventional microbiocides, preferred are cationic microbiocides, biguanide-type microbiocides, halogenated diphenyl ethers and analogues thereof, as suitable microbiocides for the present invention. Of these compounds, more preferred is at least one compound selected from the group consisting of cetylpyridinium hydrochloride, chlorhexidine, trichlosan and irgasan, or a mixture of two or more of these compounds.

More preferably, the caries-detecting composition of the invention still has some additional activity even in the stage of treatment after the removal of the caries-affected portion. Specifically, a polymerizable antimicrobial compound having both an antimicrobial group and a polymerizable group in the molecule does not interfere with the subsequent application of a dental adhesive to the surface of the tooth, even though it remains on the surface of the dentin, and, in addition, the antimicrobial compound copolymerizes with the adhesive to reinforce the adhesive layer during the restorative operation. Being different from other antimicrobial compounds that do not polymerize but remain as they are, the present polymerizable antimicrobial compound remains in the restorative material while being chemically bonded to the material after the dental treatment. Considering adhesion durability, therefore, the polymerizable antimicrobial compound is expected to exhibit remarkably safe effects. In addition, a compound of this type is further expected to modify the surface of the dentin so that it is more compatible with dental adhesives. The present inventors have found that, as an antimicrobial compound of this type, preferred are one or more polymerizable antimicrobial compounds having a (meth)acryloyl or styryl group and a quaternary ammonium salt group in the molecule, which are represented by formula 1 through formula 4.

SUMMARY OF THE INVENTION

Accordingly, one object of the present invention is to provide an antimicrobial caries-detecting composition.

Briefly, this object and other objects of the present invention as hereinafter will become more readily apparent can be attained by an antimicrobial caries-detecting composition which comprises water and/or a water-miscible solvent, a dye capable of staining the caries-infected part of teeth, and at least one dentally effective antimicrobial agent.

DETAILED DESCRIPTION OF THE PREFERRED EMBODIMENTS

In one aspect of the antimicrobial, caries-detecting composition the antimicrobial agent is selected from the group consisting of cationic microbiocides, biguanide microbiocides and halogenated diphenyl ether microbiocides.

In a second major aspect of the invention the antimicrobial agent is at least one polymerizable antimicrobial agent selected from the group consisting of compounds having a (meth)acryloyl or styryl group and a quaternary ammonium salt group in the molecule and is represented by the following formulas 1, 2, 3 and 4:

$$H_2C=C(R^1)-C(O)-X-R^2-Y \qquad (1)$$

wherein $R^1$=H or $CH_3$, $R^2$=alkylene group of $C_2$–$C_{18}$ carbons

X=O, S, or NH,

Page 11, paragraph beginning at line 2 to line 5, please amend to read as follows.

$R^3$=H or a $C_1$–$C_{18}$ alkyl group;

$R^4$=$CH_3$, $CH_2CH_3$, or $CH_2CH_2OH$;

Z=F, Cl, Br, or I;

$$H_2C=C(R^5)-C(O)-X-R^6-)_2-Y' \qquad (2)$$

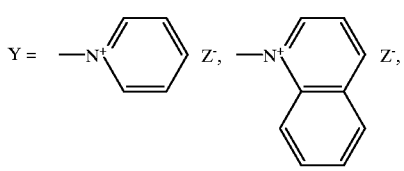

-continued

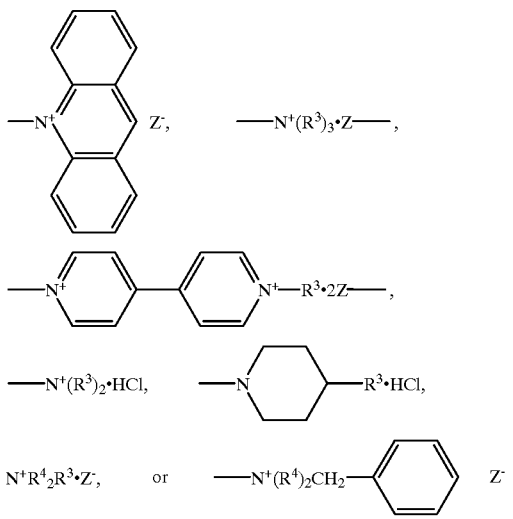

wherein
R³—H or a group of $C_1$–$C_{18}$;
R⁴—$CH_3$, $CH_2CH_3$, or $CH_2CH_2OH$;
Z=F, Cl, Br, or I;

$$[H_2C=C(R^5)-C(O)-X-R^6-]_2-Y' \quad (2)$$

wherein
R⁵=H or $CH_3$,
R⁶=alkylene group of $C_2$–$C_{12}$,
X=O, S, or NH,

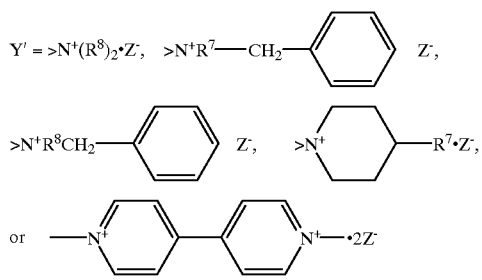

wherein
R⁷=H or alkyl group of $C_1$–$C_{18}$;
R⁸=$CH_3$, $CH_2CH_3$, or $CH_2CH_2OH$;
Z=F, Cl, Br, or I;

$$H_2C=C(R^9)-C_6H_4-R^{10}-Y \quad (3)$$

wherein
R⁹=H or $CH_3$,
R¹⁰ alkylene group of $C_2$–$C_{12}$,
Y=the same as Y in formula (1);

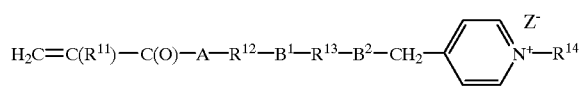

wherein
R¹¹=H or $CH_3$,
R¹²=alkylene group of $C_1$–$C_{12}$,
R¹³=alkylene group of $C_1$–$C_{12}$,
R¹⁴=alkyl group of $C_{12}$–$C_{22}$,
A=O, S, or NH,
B¹, B²=the same or different groups selected from
—CO—, $CO_2$—, —O—, —S—, —OCONH— and —$NHCO_2$—,
Z=F, Cl, Br, or I.

Suitable examples of the microbicides which are useful in the antimicrobial caries-detecting composition of the invention include cationic microbiocides of various quaternary ammonium salts, of which is preferred is cetylpyridinium hydrochloride. Also preferred are biguanide microbiocides, of which more preferred are various salts of chlorhexidine. Other preferred microbiocides are halogenated diphenyl ethers and their analogue compounds, of which especially preferred are trichlosan, irgasan, hexachlorophene, and the like. Other suitable microbiocides of the invention include thymol, clove oil, homosulfamine, nitrofurazone, sulfonamide preparations, nitrofurazone derivatives, acridine-type dyes, formalin preparations, alexidine, cetapron, metafen, sulfonamide, and the like. Among those especially preferred are trichlosan, irgasan, chlorhexidine and cetylpyridinium hydrochloride.

Suitable examples of the polymerizable antimicrobial agents for use in the invention include quaternary ammonium salts having a (meth)acryloyl group or a styryl group, as those of formula 1, and polymerizable antimicrobial compounds having a (meth)acryloyloxy group and a pyridinium salt group, as those of formula 2. The term, quaternary ammonium salt as referred to herein includes quaternary ammonium salts in the narrow sense and pyridinium salts.

Especially preferred compounds are: methacryloyloxydodecylpyridinium bromide, methacryloyloxyhexadecylpyridinium bromide, methacryloyloxyoctadecylpyridinium bromide, methacryloyloxydodecylpyridinium chloride, methacryloyloxyhexadecylpyridinium chloride, methacryloyloxyoctadecylpyridinium chloride, N,N-dimethacryloyloxyethyllaurylbenzylammonium bromide, N,N-dimethacryloyloxyethyllaurylbenzylammonium chloride, methacryloyloxyethyl[4-N-octadecylpyridinylmethyl]succinate bromide, methacryloyloxyethyl[4-N-octadecypyridinylmethyl]succinate chloride, methacryloyloxyethyl[4-N-hexadecylpyridinylmethyl]succinate bromide, methacryloyloxyethyl[4-N-hexadecylpyridinylmethyl]succinate chloride, methacryloyloxyethyl[4-N-dodecylpyridinylmethyl]succinate bromide, methacryloyloxyethyl[4-N-dodecylpyridinylmethyl]succinate chloride, hexadecyl[4-3-(5-methacryloyloxy)valeroyloxy)propyl]pyridinium bromide, hexadecyl[4-(12-methacryloylamino)dodecanoyloxy-methyl]pyridinium chloride, and the like.

Other suitable compounds include 4-vinylbenzylmethyldodecylammonium chloride, 4-vinylbenzylmethylhexadecylammonium chloride, 2-styrylethylmethyldodecylammonium chloride, 2-styrylethylmethylhexadecylammonium chloride, and the like.

However, antibiotics of some types such as sodium azide, phenol, cresol, hydrogen peroxide, iodoform, hypochlorous acid and the like, as microbiocides, are unsuitable for the composition of the invention, since they easily decompose in the composition or will decompose or denature the dye existing in the composition. Further, when they remain on the surface of the dentin, they will probably interfere with the subsequent polymerization of the radical polymerizable composition.

The dye which is used in the antimicrobial caries-detecting composition of the invention must be soluble in the solvent(s), and is capable of visually indicating the portion of the tooth into which the composition has penetrated. In addition, the dye must not be removable from the portion of the tooth it penetrates, even when the portion is rinsed with water. Preferably, the color of the dye is clearly differentiated from that of the natural dentin, and is capable of forming a striking contrast between its color and the color of the natural dentin. Accordingly, preferred are deep color dyes such as red, blue, violet or black dyes. Examples of such dyes include basic fuchsine, eosine, erythrosine, acidic fuchsine, safranine, rose bengale, Phloxine BK, acid red, fast acid magenta, Phloxine B, Fast Green FCF, Rhodamine B, gentian violet, sodium copper chlorophyll, laccaic acid, cochineal, and shisonin. One or more of those dyes are usable in the invention.

It is noted that Phloxine BK has the CI number 5410 and is also known as Acid Red 92. Phloxine B has the same designation. Fast Green FCF has the CI number 42053 Rhodamine B has the CI number 45170. The CI number is the Color Index number The dye concentration in the composition preferably ranges from 0.1–2% by weight, more preferably from 0.1–1% by weight. If it is less than the defined range, the dye does not satisfactorily stain the intended region. However, if it is greater than the defined range, the dye stains even the second decalcified layer and even further the healthy area, which obviously makes the determination of the infected area more difficult.

The solvent for the composition of the invention must be so selected that not only does it dissolve the dye and the microbiocide in the composition, but also reduces the viscosity of the composition to facilitate the penetration of the composition into the infected dentin. Preferred solvents include those which are water-miscible solvents which are easily miscible with water in any ratio to give a uniform solution. Desirably, the water-miscible solvent compound has not more than 10 carbon atoms, has a polar group, and has a viscosity of not larger than 20 cps. Especially preferred are organic mono-, di- or tri-hydroxy compounds having from 2 to 10 carbon atoms. These solvents enhance the penetration of the dye into the caries area to promote the clear coloration of the caries area.

Suitable examples of solvent compounds include ethanol, ethylene glycol, n-propanol, isopropanol, 1,2-propylene glycol, 1,3-propylene glycol, 1,2-butanediol, 1,3-butanediol, 1,4-butanediol, isobutyl alcohol, n-amyl alcohol, isoamyl alcohol, diethylene glycol, triethylene glycol, tetraethylene glycol, ethylene glycol monomethyl ether, ethylene glycol monoethyl ether, ethylene glycol monobutyl ether, ethylene glycol monoacetate, diethylene glycol monoethyl ether, diethylene glycol monobutyl ether, diethylene glycol monoacetate, triethylene glycol monomethyl ether, triethylene glycol monoethyl ether, glycerin, and the like. of these, preferred are propylene glycol and triethylene glycol, since they produce good results.

Other organic solvents useful in the invention include tetrahydrofuran. dimethylformamide, dimethylsulfoxide, dioxane, acetone and dimethoxyethane. Phenol cannot be used in the invention, since it is too toxic. organic amines, despite their good ability to fix dyes, are unsuitable for the invention, since they emit an offensive odor and they are harmful to the human body. Hydrocarbons are also unsuitable, since they poorly dissolve dyes and their ability to fix dyes is much inferior to the dye-fixing ability of water.

As has been mentioned herein above. The organic solvents may be used in combination with water, and one or more of them may be used in a mixture. The blending ratio of the solvents may be suitably determined, depending on the solvents which are blended.

The composition of the invention can be prepared easily. For example, a predetermined amount of the dye and a predetermined amount of the microbiocide may be added to the organic solvent, distilled water or a mixture thereof, and the combined materials are stirred and dissolved at room temperature or under mild heating. Alternatively, an excessive amount of the dye and an excessive amount of the microbiocide are first dissolved in the organic solvent, distilled water or a mixture thereof, and then the organic solvent, distilled water or mixture thereof is added to the resulting solution to dilute it to a desired concentration just before its use. Depending on the combination of the microbiocide and the solvent, the microbiocide may be difficult to dissolve in the solvent. In such a case, any known conventional surfactant may be added to the mixture to give a uniform composition.

To apply the antimicrobial caries-detecting composition of the invention to the cavity of the caries-infected tooth of a patient, the composition is placed in a container equipped with a thin long nozzle, and a small amount of the composition is dropped onto the cavity through the nozzle. One to 10 seconds after this application, the cavity is rinsed with water. By this simple operation, just the first ring of decalcified layer is clearly stained with the composition, while the second decalcified layer and the non-infected dentin are hardly stained. As a result, the portion infected with cariogenic microbes can be accurately detected, while, at the same time, the bacteria existing in the infected area are killed or inactivated.

By using the antimicrobial caries-detecting composition of the invention, caries-infected dentin can be removed from the teeth while preventing the cavity and the area around it from being contaminated with highly contaminated tissue pieces that may be scattered during the removal of the infected portion. Accordingly, the antimicrobial caries-detecting composition of the invention provides safer treatment of caries by not allowing failure to remove infected dentin and by not allowing re-contamination of the treated tooth with the removed infected dentin.

Having now generally described the invention, a further understanding can be obtained by reference to certain specific examples which are provided herein for purpose of illustration only and are not intended to be limiting unless otherwise specified.

Various types of dyes, antimicrobial agents and organic solvents usable of the Invention are mixed and stirred at room temperature to prepare various detecting compositions as shown in Table 1. These compositions were applied to the cross-section of caries infected teeth extracted from patients, and tested for their stain differentiability and microbiocidability.

For stain differentiability, each sample was applied to the cross-section of the caries-infected tooth. About 5 seconds after application, the applied area was rinsed with water and observed as to whether the caries-infected portion could be clearly differentiated from the healthy dentin portion on the basis of the intrinsic color difference and the difference in hardness between the two parts. From these data, the samples were evaluated in accordance with the following criteria:

++: The caries-infected portion was clearly stained.

+: The caries-infected portion was stained.

+−: The caries-infected portion was slightly stained.

−: The caries-infected portion was hardly stained.

For the microbiocidability, each sample was applied to the caries-infected portion of the tooth. Ten seconds after the application, the tooth was rinsed with water, and the stained portion and the portion deeper than the stained part were ground with a carbide bar attached to an air turbine. The resulting powdered teeth were placed in a germ-free BHI (brain heart infusion) broth medium, and the resulting material was treated with ultrasonic vibrations for 10 minutes, and incubated therein overnight. The growth of the cariogenic bacteria was observed by the light absorbance of the resulting culture. From the data thus obtained, the samples were evaluated in accordance with the following criteria:

++: The growth of bacteria in the stained powdered teeth was inhibited, and no bacteria grew in the non-stained teeth.

+−: The growth of bacteria in the stained powdered teeth was inhibited, but bacteria grew in the non-stained teeth.

−−: The growth of bacteria in the stained powdered teeth was not inhibited at all, and bacteria grew in the non-stained teeth. Table 1

[Advantages of the Invention]

Table 1 below shows that the antimicrobial caries-detecting composition of the invention is effectively useful in the dental treatment of caries for the removal of cariogenic microbes that may be left in the cavity of caries-infected teeth. Even if some cariogenic microbes are left in the cavity, the antimicrobial caries-detecting composition can completely kill the remaining microbes, thereby effectively inhibiting the dental pulp irritation and the secondary caries which are caused by the remaining microbes.

the solvent in a concentration of 0.1 to 2 wt % capable of selectively staining the caries-infected portion of teeth, and (iii) at least one antimicrobial agent dissolved in the solvent selected from the group consisting of cationic microbiocides, biguanide microbiocides and halogenated diphenyl ether microbiocides.

2. The antimicrobial caries-detecting composition according to claim 1, wherein said antimicrobial agent is at least one member selected from the group consisting of trichlosan, irgasan, chlorhexidine and cetylpyridinium hydrochloride.

3. The antimicrobial caries-detecting composition according to claim 1, wherein said antimicrobial agent is at least one member selected from the group consisting of thymol, clove oil, homosulfamine, nitrofurazone, sulfonamides, acridine dyes, formalin, alexidine, cetapron, and metafen.

4. The antimicrobial caries-detecting composition according to claim 1, wherein said dye concentration ranges from 0.1–1 wt %.

5. A The antimicrobial caries-detecting composition according to claim 1, wherein said dye is basic fuchsine, eosine, erythrosine, acidic fuchsine, safranine, rose bengale, acid red, fast acid magenta, CI5410, CI42053, CI 45170, gentian violet, sodium copper chlorophyll, laccaic acid,

TABLE 1

| | Dye (1%) | Solvent | Microbicidal Agent (1%) | Stain Differentiability | Microbicidability |
|---|---|---|---|---|---|
| Example 1 | Phloxine BK | Propylene Glycol | Trichlosan | ++ | ++ |
| Example 2 | Acid Red | Propylene Glycol | Trichlosan | ++ | ++ |
| Example 3 | Fast Acid Magenta | Ethylene Glycol | Trichlosan | + | +− |
| Example 4 | Phloxine B | Ethylene Glycol | Trichlosan | + | +− |
| Example 5 | Fast Green FCF | Propylene Glycol | Chlorhexidine * | + | +− |
| Example 6 | Rhodamine B | Propylene Glycol | Chlorhexidine * | ++ | ++ |
| Example 7 | Rhodamine B | Triethylene Glycol | Chlorhexidine * | ++ | ++ |
| Example 8 | Basic Fuchsine | Ethanol/Water = 50/50 | Pyridinium Salt ** | ++ | ++ |
| Example 9 | Eosine | 1,3-Hexanediol/Water = 50/50 | Pyridinium Salt ** | ++ | ++ |
| Example 10 | Acidic Fuchsine | Ethylene Glycol | Pyridinium Salt ** | ++ | ++ |
| Example 11 | Basic Fuchsine | Propylene Glycol | Pyridinium Salt ** | ++ | ++ |
| Example 12 | Basic Fuchsine | Propylene Glycol | MDPB *** | ++ | ++ |
| Example 13 | Basic Fuchsine | Propylene Glycol | APSM-16 **** | ++ | ++ |
| Comparative Example 1 | Basic Fuchsine | Aqueous Ethanol | None | ++ | −− |
| Comparative Example 2 | None | Aqueous Ethanol | Irgasan | −− | ++ |
| Comparative Example 3 | None | Propylene Glycol | Trichlosan | −− | ++ |

*: Chlorhexidine Acetate
**: Cetylpyridinium Hydrochloride
***: Methacryloyloxydodecylpyridinium bromide
****: Methacryloyloxyethyl (4-N-hexadecylpyridinylmethyl) succinate bromide The disclosures of priority Japanese Application Nos. 9-38681 and 9-45634 filed Feb. 24, 1997 and February 28, 1997 respectively are hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and intended to be secured by Letters Patent is:

1. An antimicrobial caries-detecting composition, which is a solution consisting of:

(i) a solvent which is water, a water-miscible organic solvent or a combination thereof, (ii) a dye dissolved in cochineal or shisonin, wherein the CI number is the color index number.

6. The antimicrobial caries-detecting composition according to claim 1, wherein said solvent is ethanol, ethylene glycol, n-propanol, isopropanol, 1,2-propylene glycol, 1,3-propylene glycol, 1,2-butanediol, 1,3-butanediol, 1,4-butanediol, isobutyl alcohol, n-amyl alcohol, isoamyl alcohol, diethylene glycol, triethylene glycol, tetraethylene glycol, ethylene glycol monomethyl ether, ethylene glycol monoethyl ether, ethylene glycol monobutyl ether, ethylene glycol monoacetate, diethylene glycol monoethyl ether, diethylene glycol monobutyl ether, diethylene glycol monoacetate, triethylene glycol monomethyl ether, triethylene glycol monoethyl ether or glycerin.

* * * * *

UNITED STATES PATENT AND TRADEMARK OFFICE
CERTIFICATE OF CORRECTION

PATENT NO.    : 6,337,357 B1
DATED         : January 8, 2002
INVENTOR(S)   : Fukunishi et al.

It is certified that error appears in the above-identified patent and that said Letters Patent is hereby corrected as shown below:

<u>Title page,</u>
Item [30], the Foreign Application Priority information should read:

-- [30]         Foreign Application Priority Data
        Feb. 24, 1997    (JP) ......................... 9-38681
        Feb. 28, 1997    (JP) ......................... 9-45634 --

Signed and Sealed this

Twentieth Day of August, 2002

Attest:

Attesting Officer

JAMES E. ROGAN
*Director of the United States Patent and Trademark Office*